United States Patent
Herold (10) Patent No.: US 9,295,434 B2
(45) Date of Patent: Mar. 29, 2016

(54) DYNAMIC COLLIMATION

(75) Inventor: Mark Douglas Herold, Stow, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 187 days.

(21) Appl. No.: 14/232,293

(22) PCT Filed: Jul. 4, 2012

(86) PCT No.: PCT/IB2012/053417
§ 371 (c)(1),
(2), (4) Date: Jan. 13, 2014

(87) PCT Pub. No.: WO2013/011403
PCT Pub. Date: Jan. 24, 2013

(65) Prior Publication Data
US 2014/0177782 A1 Jun. 26, 2014

Related U.S. Application Data (60) Provisional application No. 61/508,180, filed on Jul. 15, 2011.

(51) Int. Cl.
*A61B 6/06* (2006.01)
*H05G 1/26* (2006.01)
*A61B 6/03* (2006.01)
*A61B 6/00* (2006.01)

(52) U.S. Cl.
CPC . *A61B 6/06* (2013.01); *A61B 6/032* (2013.01); *A61B 6/488* (2013.01); *A61B 6/542* (2013.01); *A61B 6/469* (2013.01)

(58) Field of Classification Search
CPC .......... A61B 6/032; A61B 6/027; A61B 6/06; A61B 6/4085; A61B 6/4028; A61B 6/466; A61B 6/542; A61B 6/4476; A61B 6/488; A61B 6/022; H05G 1/26; H05G 1/52; G01N 23/046
USPC ......... 378/19, 11, 15, 150, 4, 151, 16, 8, 147, 378/152, 156, 157, 20, 205, 98.12, 98.8
See application file for complete search history.

(56) References Cited

U.S. PATENT DOCUMENTS

| | | | |
|---|---|---|---|
| 4,315,157 A | 2/1982 | Barnes | |
| 5,550,886 A * | 8/1996 | Dobbs | A61B 6/032 378/19 |
| 5,625,661 A * | 4/1997 | Oikawa | A61B 6/022 378/15 |
| 6,298,117 B1 * | 10/2001 | Hampel | A61B 6/032 378/147 |
| 6,322,248 B1 * | 11/2001 | Yanagita | A61B 6/032 378/11 |
| 6,501,828 B1 | 12/2002 | Popescu | |
| 7,113,569 B2 * | 9/2006 | Okumura | A61B 6/032 378/150 |
| 7,340,033 B2 * | 3/2008 | Mollus | A61B 6/06 378/147 |
| 7,697,658 B2 | 4/2010 | Wang et al. | |

(Continued)

FOREIGN PATENT DOCUMENTS

| | | |
|---|---|---|
| EP | 1149558 A2 | 10/2001 |
| WO | 2009141766 A2 | 11/2009 |

*Primary Examiner* — David A Vanore (57) ABSTRACT

A method includes performing a three dimensional volume scan of a region of interest located in a portion of an object or subject in an examination region, including dynamically collimating a radiation beam used to perform the scan so that a geometry and/or location of the radiation beam tracks, during the scan, to a geometry and/or location of the region of interest, wherein the region of interest is a sub-region of the portion of the object or subject in the examination region.

18 Claims, 5 Drawing Sheets

(56) References Cited

U.S. PATENT DOCUMENTS

| | | | |
|---|---|---|---|
| 7,706,500 B2 * | 4/2010 | Kondo | A61B 6/032 378/15 |
| 7,983,385 B2 * | 7/2011 | Heuscher | A61B 6/032 378/11 |
| 8,401,144 B2 * | 3/2013 | Forthmann | A61B 6/032 378/19 |
| 8,467,494 B2 * | 6/2013 | Brown | A61B 6/032 378/4 |
| 8,571,172 B2 * | 10/2013 | Dafni | A61B 6/032 378/11 |
| 8,897,413 B2 * | 11/2014 | Heuscher | A61B 6/032 378/15 |
| 2003/0076927 A1 * | 4/2003 | Nakashima | A61B 6/032 378/65 |
| 2011/0013742 A1 | 1/2011 | Zaiki et al. | |
| 2011/0033024 A1 | 2/2011 | Dafni et al. | |
| 2011/0058645 A1 * | 3/2011 | Heuscher | A61B 6/032 378/16 |

\* cited by examiner

DYNAMIC COLLIMATION

CROSS REFERENCE TO RELATED APPLICATIONS

This application is a national filing of PCT application Serial No. PCT/IB2012/053417, filed Jul. 4, 2012, published as WO 2013/011403 A1 on Jan. 24, 2013, which claims the benefit of U.S. provisional application Ser. No. 61/508,180 filed Jul. 15, 2011, which is incorporated herein by reference.

FIELD OF THE INVENTION

The following generally relates to dynamically collimating, during scanning, radiation emitted by a radiation source of an imaging system based on a geometry of a region of interest in a portion of an object or subject being scanned and is described with particular application to computed tomography (CT). However, the following is also amenable to other imaging modalities.

BACKGROUND OF THE INVENTION

A computed tomography (CT) scanner generally includes a rotating gantry rotatably supported by a stationary gantry. The rotating gantry is configured to rotate about an examination region and supports an x-ray tube that rotates therewith. The x-ray tube is configured to emit ionizing radiation at least in a direction towards the examination region. A source collimator collimates the radiation, producing a radiation beam, having a predetermined shape, which traverses the examination region and a portion of an object or subject in the examination region. A subject support supports the object or subject in the examination region. A detector array, located across the examination region and opposite the x-ray tube, detects radiation traversing the examination region and the object or subject and generates projection data indicative thereof. A reconstructor reconstructs the projection data and generates three dimensional volumetric image data.

Typically, before the above-discussed three dimensional volume scan of the object or subject, one or more pre-scans (e.g., surview, scout, pilot, etc. scans) are performed. For a typical pre-scan, the rotating gantry and hence the x-ray tube is rotated to, if not already at, and held or maintained at a static angular position. Then, the subject support translates the object or subject through the examination region while the x-ray tube emits radiation and the detector detects radiation. The reconstructor reconstructs a two-dimensional (2D) projection image for each pre-scan from the acquired data. The 2D projection image(s) is used to facilitate creating an imaging examination plan for the three dimensional volume scan of the object or subject. This has included using the 2D projection image to identify a region of interest (ROI), identify a start scan location, and identify an end scan location (or scan length) to scan the ROI.

Figure 1:
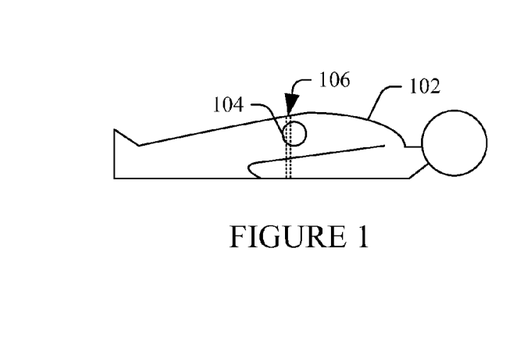
FIGS. 1 and 2 schematically illustrate a patient and a region of interest within the patient to be scanned with an imaging system.
Figure 2:
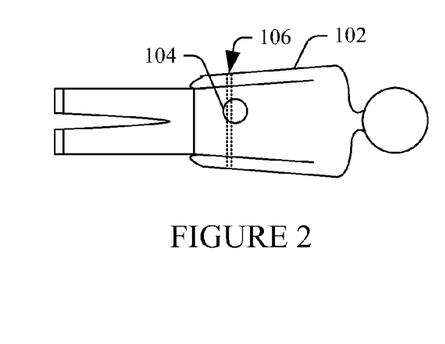
Figure 3:
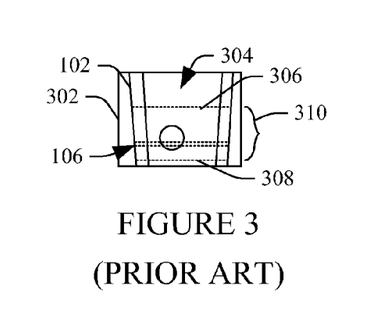
FIG. 3 schematically illustrates a 2D projection image and 3D volume scan plan planed based on the 2D projection image.

By way of non-limiting example, FIGS. 1 and 2 respectively show a patient 102 and a ROI 104 in the patient 102 from a side view and a front view of the patient 102. Note that the ROI 104 is depicted as a sphere in this example. However, it is to be understood that the ROI 104 can be other geometrical shapes, including, but not limited to irregular. FIG. 3 shows an example 2D projection image 302 with anatomical structure outside of the ROI 104 visually removed from within the patient 102 for clarity of this discussion. FIG. 3 also shows an imaging plan 304 for a three dimensional volume scan of the ROI 104, including a start scan location 306 and an end scan location 308 (or a scan length 310).

Figure 4:
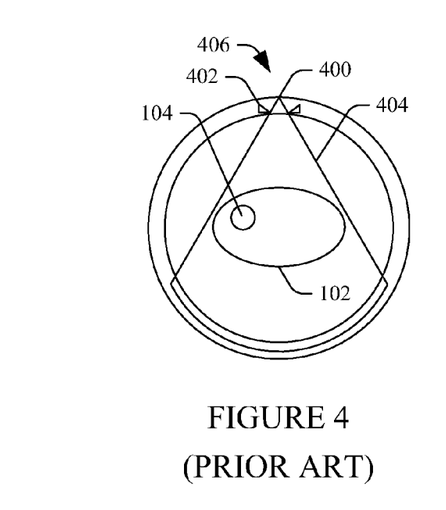
FIGS. 4, 5 and 6 schematically illustrate execution of the 3D volume scan plan based on prior art source collimation.
Figure 5:
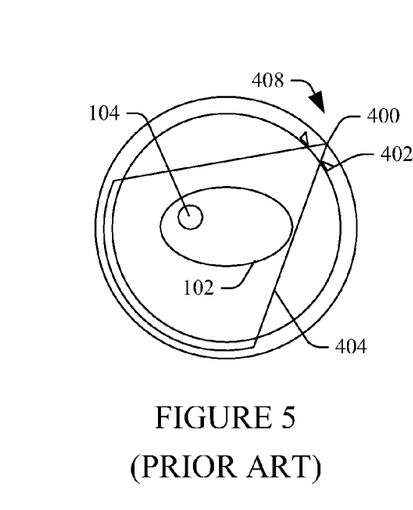
Figure 6:
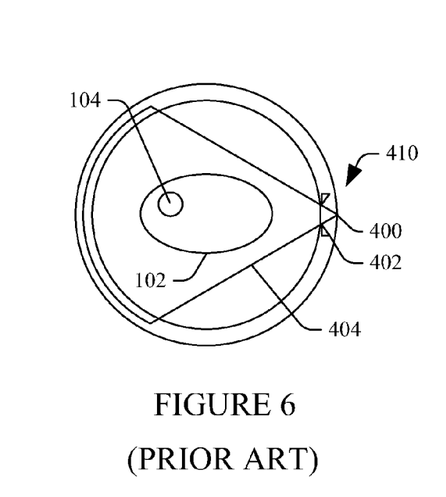

FIGS. 4, 5 and 6 respectively shows a radiation source 400, a collimator 402 with a fixed collimation, and a corresponding radiation beam 404 at three different view angles 406, 408, and 410 for a volume scan of the ROI 104 in the patient 102 based on the plan 304 in FIG. 3. The slice shown in FIGS. 4, 5 and 6 corresponds to a slice 106 shown in FIGS. 1, 2 and 3.

Note that in this example, the size of the ROI 104 is less than one tenth of the anatomical structure irradiated each view during the scan. Thus, the patient 102 receives substantially more dose than that needed to image the ROI 104 in each view. Unfortunately, CT scanners emit ionizing radiation, which may damage or kill cells and/or increase the risk of cancer. As such, there is an unresolved need for other approaches for scanning a ROI within a patient.

SUMMARY OF THE INVENTION

Aspects of the present application address the above-referenced matters and others.

According to one aspect, a method includes performing a three dimensional volume scan of a region of interest located in a portion of an object or subject in an examination region, including dynamically collimating a radiation beam used to perform the scan so that a geometry and/or location of the radiation beam tracks, during the scan, to a geometry and/or location of the region of interest, wherein the region of interest is a sub-region of the portion of the object or subject in the examination region.

In another aspect, an imaging system includes a radiation source that emits radiation in a direction towards an examination region. The imaging system further includes a collimator having at least one collimating member that collimates the emitted radiation, producing a radiation beam having a predetermined shape and that traverses the examination region. The collimator dynamically adjusts a geometry and/or location of the radiation beam for one or more view angles in accordance with a geometry and/or location of a region of interest in a portion of an object or subject disposed in the examination region. The region of interest is a sub-region of the portion of the object or subject disposed in the examination region. The system further includes a detector array, located opposite the source and across the examination region, that detects radiation traversing the examination region and generates a signal indicative of the detected radiation.

In another aspect, a method for optimizing dose in an imaging examination includes identifying a region of interest of object or subject to scan in a two dimensional projection image of the object or subject, collimating emitted radiation so that radiation traversing the examination region substantially only irradiates the region of interest while not irradiating a remainder portion of the object or subject, and adjusting the collimation as needed so that the radiation continues to substantially only irradiate the region of interest while not irradiating the remainder portion for the imaging examination.

Still further aspects of the present invention will be appreciated to those of ordinary skill in the art upon reading and understanding the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 7:
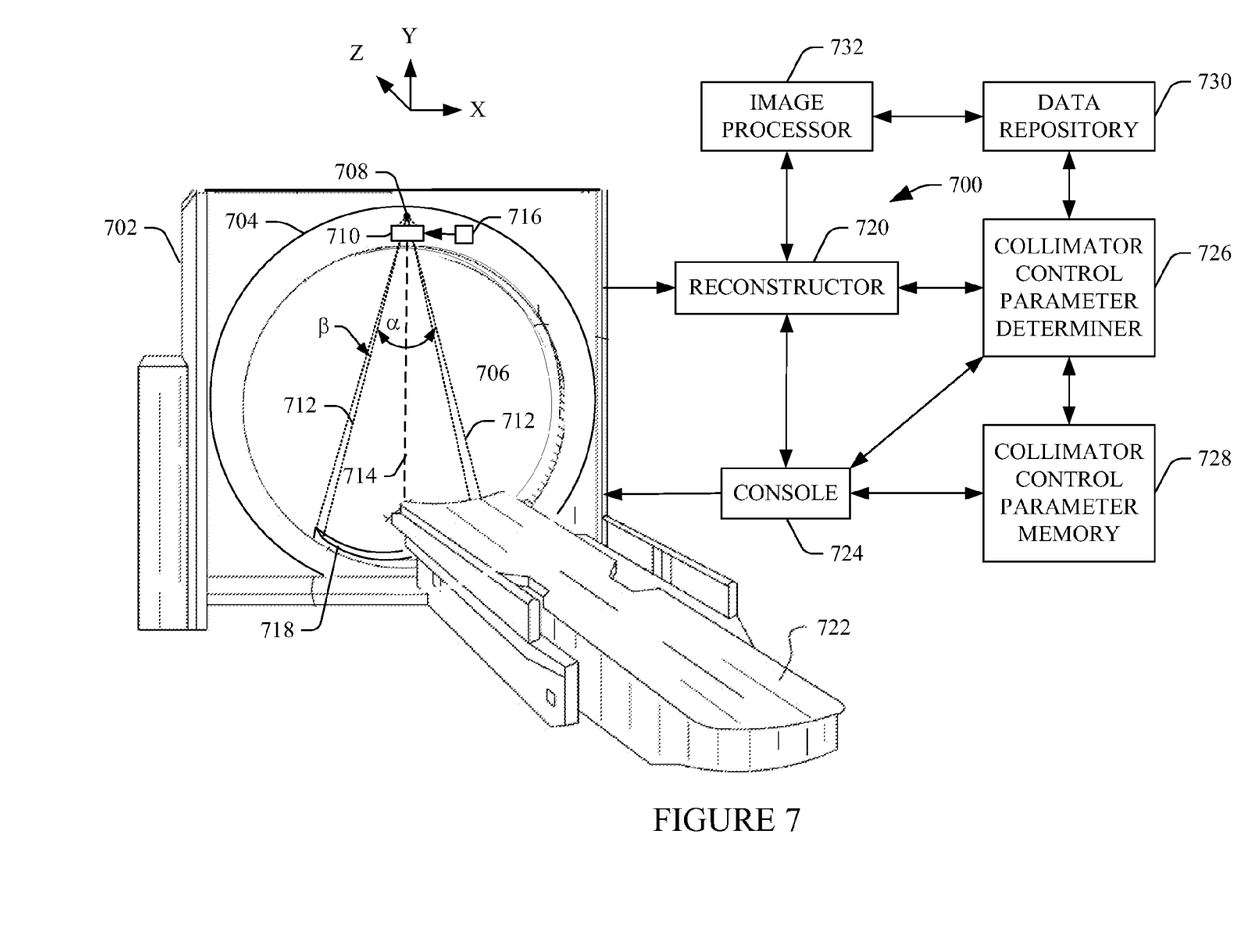
FIG. 7 schematically illustrates an example imaging system in connection with a collimator control parameter determiner.

FIG. 7 illustrates an imaging system 700 such as a computed tomography (CT) scanner.

The imaging system 700 includes a stationary gantry 702 and a rotating gantry 704, which is rotatably supported by the stationary gantry 702. The rotating gantry 704 is configured to rotate around an examination region 706 about a longitudinal or z-axis.

The imaging system 700 further includes a radiation source 708, such as an x-ray tube, which is supported by and rotates with the rotating gantry 704 around the examination region 706. The radiation source 708 is configured to emit ionizing radiation at least in a direction towards the examination region 706.

The imaging system 700 further includes a collimator 710 that collimates the emitted radiation and produces a radiation beam 712 having a pre-determined shape (e.g., fan, wedge, cone, or otherwise) that traverses the examination region 706 and a portion of an object or subject therein. The collimator 710 is configured to collimate the radiation to define a geometry and/or a location of the beam in x (transverse) and/or z (longitudinal) directions. The beam geometry is determined in the x direction based on an angle α between outer rays of the beam along the x direction and in the z direction based on an angle β between outer rays of the beam along the z direction. As used herein, the beam location is with reference to an imaginary line 714 extending perpendicularly from the source 708 through a center of the examination region 706.

As described in greater detail below, the illustrated collimator 710 is configured to dynamically change the geometry and/or location of the beam during scanning, for example, to track a geometry and/or location of the radiation beam to a geometry and/or location of the a region of interest (ROI) within an object or subject being scanned. This includes, but is not limited to, tracking the geometry and/or location of the radiation beam to periodically moving anatomy (e.g., the heart, lungs, etc.) based on a signal (e.g., obtain via EKG, respiratory belt, etc.) indicative of the movement of the periodically moving anatomy. In one instance, tracking the geometry and/or location of the radiation beam 712 as such produces a beam that traverses the object or subject through paths that substantially only traverse the ROI, while mitigating traversing paths that do not traverse the ROI, reducing overall patient dose relative to a configuration in which the collimator 710 collimates the beam 712 such that the beam traverses through the object or subject through paths that traverse the entire portion of the object or subject in the examination region 706 (e.g., as shown in FIGS. 4, 5 and 6).

The imaging system 700 further includes a collimator controller 716 that controls the collimator 710. The illustrated controller 716 controls the collimator 710 to define the beam geometry and/or location based on collimator control parameters.

The imaging system 700 further includes a radiation sensitive detector array 718, which is also supported by and rotates with the rotating gantry 704, and is located opposite the radiation source 708 and across the examiner region 706. Suitable detector arrays include one and two dimensional arrays respectively having a single or multiple rows of detector elements. The detector array 718 detects radiation that traverses the examination region 706 and generates a signal indicative of the detected radiation.

The imaging system 700 further includes a reconstructor 720 that reconstructs the signal and generates data indicative of the examination region 706. Such data may include two dimensional (2D) projection data (e.g., one or more scout or pilot scans) and/or three dimensional 3D volumetric image data (e.g., an axial or helical scan). An example of a 3D reconstruction algorithm that can be used to reconstruct data acquired while dynamically tracking, during scanning, the geometry and/or location of the beam to a geometry and/or location of the ROI is discussed in connection with U.S. Pat. No. 7,697,658. Other reconstruction algorithms can also be employed by the reconstructor 720.

The imaging system 700 further includes a subject support 722, such as a couch, supports a subject such as a human or animal patient in the examination region 706 and is movable along the x, y and/or z-axis in coordination with the rotation of the rotating gantry 704 to facilitate pre-scan, and/or helical, axial, or other desired scanning trajectories.

The imaging system 700 further includes a general purpose computing system that serves as an operator console 724, and includes an output device such as a display and an input device such as a keyboard, mouse, and/or the like. The console 724 allows a user to operate the system 700 such as start a 2D projection pre-scan, plan a 3D volume scan, start a planned 3D volume scan, etc.

A collimator control parameter determiner 726 determines control parameters used by collimator controller 716 to control the collimator 710 to define the bean geometry and/or location. The illustrated collimator control parameter determiner 726 is configured to determine such control parameters at least based on one or more 2D projection images including a representation of the ROI. In one instance, this includes determining control parameters that will cause the collimator 710 to adjust collimation during scanning so that the geometry and/or location of the beam 712 dynamically tracks the geometry and/or location of the ROI.

The collimator control parameter determiner 726 can store determined collimator control parameters in collimator control parameter memory 728 and/or other memory, including, local, remote, distributed, and/or other memory. Parameters stored in the collimator control parameter memory 728 can also be utilized to plan subsequent 3D volume scans. Using stored parameters mitigates having to perform another 2D projection scan, which may reduce overall patient dose for the study. The collimator control parameter determiner 726 can obtain the one or more 2D projection images from the reconstructor 720 and/or a data repository 730, such as a database, a server, a picture archiving and communication system (PACS), radiology information system (RIS), a hospital information system (HIS), and/or other electronic storage device or memory.

An image processor 732 processes reconstructed image data. In one instance, this includes superimposing an image of the ROI with a previously generated image of the patient. This allows for providing an anatomical frame of reference for the ROI since the image of the ROI may not include such information with sufficient or desired detail. Alternatively, the image of the ROI may be superimposed with an image from a different patient with similar physical attributes, a graphical anatomical model, and/or other data. Additionally or alternatively, the image processor 732 may visually display the ROI image with a corresponding ROI and/or other image from a previous scan for comparative purposes, for example, for a visual observation of changes in size and/or location of the ROI, for example, in a follow-up study.

In FIG. 7, the collimator control parameter determiner 726, the collimator control parameter memory 728, the data repository 730 and the image processor 732 are shown separate from the system 700. In another embodiment, one or more of the components 726-732 can be part of the system 700, for example, part of the console 724. In either instance, one or more processors executes one or more computer readable and executable instructions encoded on computer readable storage medium such as physical memory to implement the one or more of the components 726-732. Additionally or alternatively, at least one of the computer readable and executable instructions executed by the one or more processors is carried by a signal or carrier wave.

The system 700 is described above in connection with a third generation CT scanner in which the radiation sensitive detector array 718 is an arc shaped detector array that rotates in coordination with the rotating radiation source 708. However, it is to be understood that fourth generation CT scanners are also contemplated herein. Generally, with a fourth generation CT scanner, the radiation sensitive detector array is a closed ring that is held at a static position and does not rotate.

Figure 8:
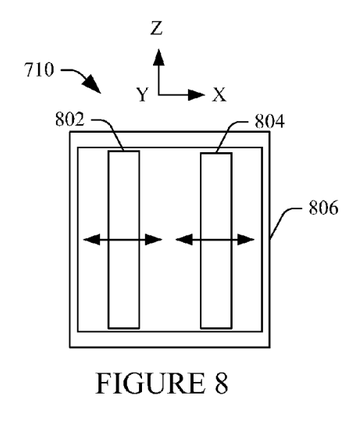
FIGS. 8, 9 and 10 schematically illustrate non-limiting examples of collimators.
Figure 9:
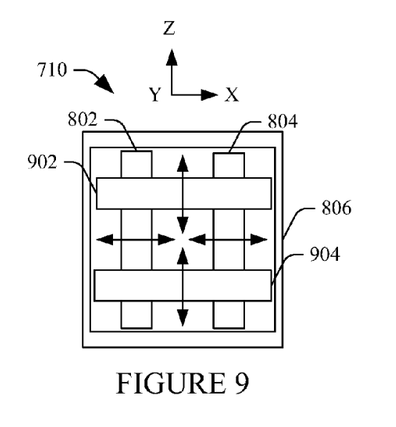
Figure 10:
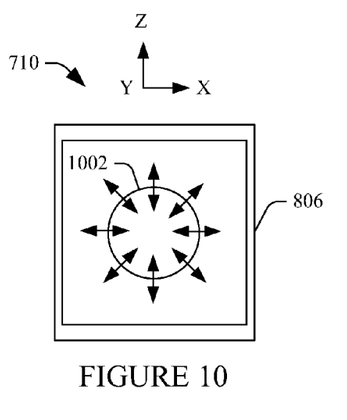

From above, the collimator 710 is configured to collimate the radiation emitted by the source 108 in the x and/or z directions to produce the radiation beam 712 having a geometry and/or location that tracks a geometry and/or location of a ROI during scanning FIGS. 8, 9 and 10 illustrate non-limiting examples of the collimator 710 looking down into the collimator 710 from the y direction into the examination region 706.

In FIG. 8, the collimator 710 includes first and second generally rectangular collimating members 802 and 804. The members 802 and 804 include radiation attenuating material and are located with respect to each other along the x direction. Each of the members 802 and 804 is movably mounted within a carriage 806 and can move along the x direction. Each of the members 802 and 804 is configured to move towards the other member 802 or 804 and away from the other member 802 or 804.

The members 802 and 804 can be moved using the same drive system or different drive systems, and can move synchronously, asynchronously, and/or individually. Optionally, the entire carriage 806 is also configured to move along the x direction. Moving the members 802 and 804 changes an aperture size (or geometry) of the beam and/or a location of the beam, and moving the carriage 806 changes a location of the beam.

FIG. 9 is substantially similar to FIG. 8, but also includes third and fourth generally rectangular collimating members 902 and 904. The members 902 and 904 include radiation attenuating material and are located with respect to each other along the z direction. Each of the members 902 and 904 is moveable mounted within the carriage 806 and can move along the z direction. Each member 902 and 904 is configured to move towards the other member 902 or 904 and away from the other member 902 or 904.

Likewise, the members 902 and 904 can be moved using the same drive system or different drive systems, and can move synchronously, asynchronously, and/or individually. Optionally, the carriage 806 is also configured to move along the z direction. Moving the members 902 and 904 changes an aperture size (or geometry) of the beam and/or a location of the beam, and moving the carriage 806 changes a location of the beam.

In FIG. 10, the collimator 710 includes an adjustable elliptically shaped collimating member 1002, which includes radiation attenuating material. The collimating member 1002 is supported by the carriage 806 and is configured to increase and decrease in diameter (or radius), which concurrently adjusts collimation in the x-z plane. Similar to FIGS. 8 and 9, the carriage 806 may also be configured to move in the x and/or z directions. Adjusting the members 1002 changes an aperture size (or geometry) of the beam, and moving the carriage 806 changes a location of the beam.

It is to be appreciated that the embodiments described in connection with FIGS. 8, 9 and 10 are non-limiting and provided for explanatory purposes, and that other known and/or other collimators and/or collimator configurations are contemplated herein.

Figure 11:
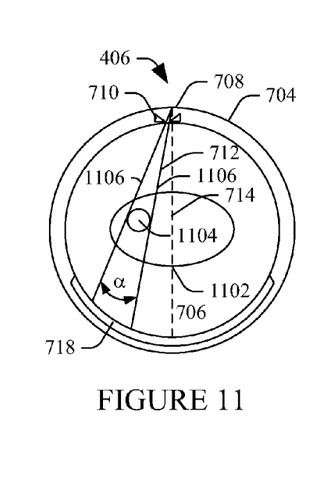
FIGS. 11, 12 and 13 schematically illustrate execution of the 3D volume scan plan based on dynamic collimation which tracks beam geometry to region of interest geometry.
Figure 12:
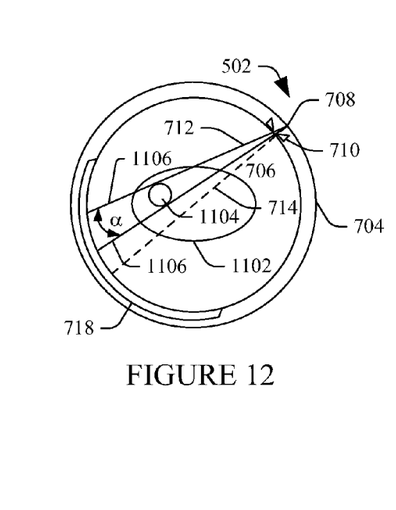
Figure 13:
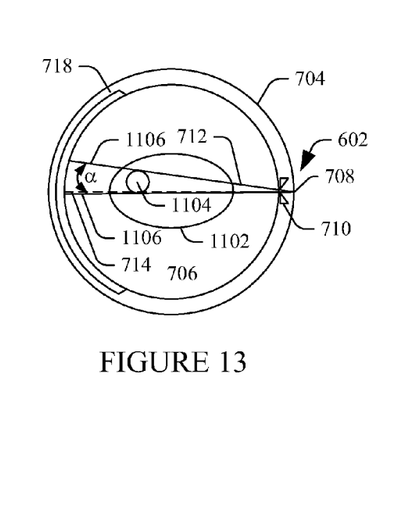

FIGS. 11, 12 and 13 respectively show the collimator 710 collimating the beam 712 so that the geometry and/or location of the beam 712 tracks a geometry and/or location of a ROI 1104 in a patient 1102, and not the entire portion of the patient 1102 in the examination region 706 (like FIGS. 4, 5 and 6). For comparative purposes, the FIGS. 11, 12 and 13 show the beam 712 at the at three different view angles 406, 502 and 602 shown in connection with FIGS. 4, 5 and 6. For clarity, the beam 712 is only shown in the x-y plane; however, it is to be understood that the beam 712 can concurrently or alternatively track the geometry and/or location of the ROI 1104 in the y-z plane. In addition, the ROI 1104 may include one or more sub-ROIs.

As can be seen in this example, the angle α and the location of the beam 712 with respect to the line 714 changes at least between the view angles in FIGS. 11, 12 and 13, and is different than that in FIGS. 4, 5 and 6. Note that the beam 712 in these figures is collimated so outer rays 1106 of the beam traverse a perimeter or just outside of the perimeter of the ROI 1104. As such, the overall dose to the subject or object 1102, relative to a scan with the beam configuration of FIGS. 4, 5 and 6, is lower, with a higher dose (e.g., full dose) to the ROI 1104, through focusing the beam 712 at the ROI 1104, and a lower dose outside of the ROI 1104, where the beam 712 is not focused.

In other embodiments, the beam angle can be adjusted so that a space or predetermined margin between the perimeter of the ROI 1104 and the outer rays 1106 is greater than that shown, but without irradiating the entire portion of the patient in the examination region 706. Of course, the beam angle can also be set so that the beam coverage is similar to that shown in FIGS. 4, 5 and 6.

Figure 14:
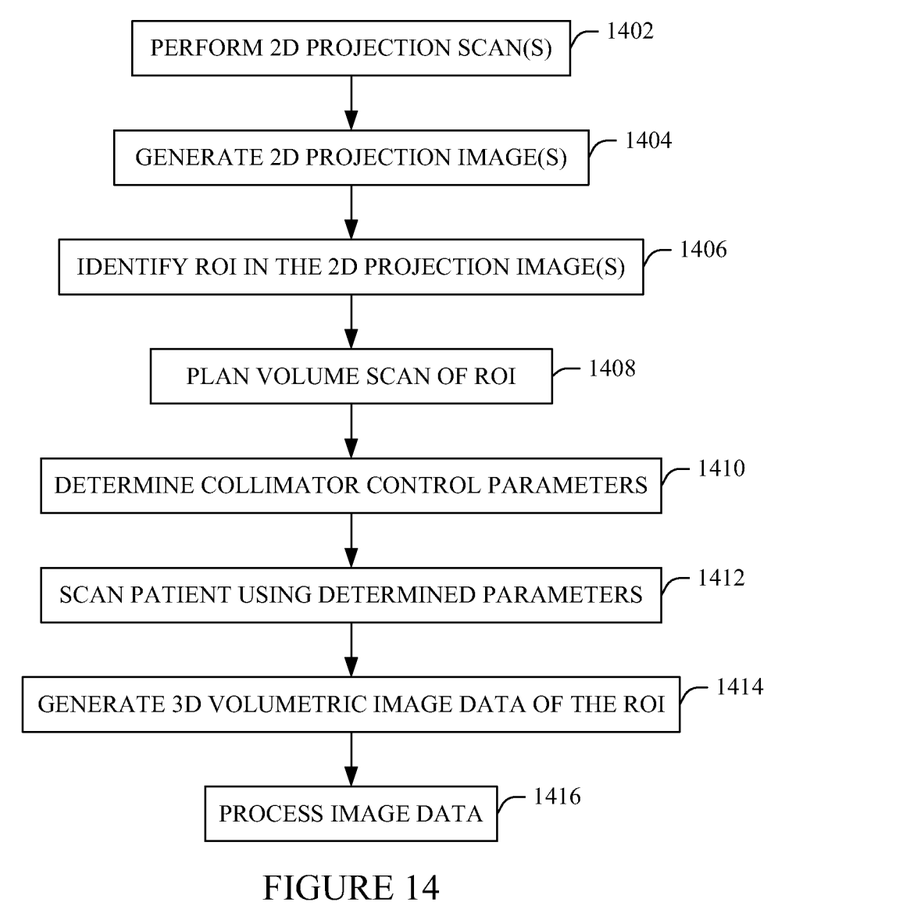
FIGS. 14, 15 and 16 schematically illustrate various methods for scanning using dynamic collimation which tracks beam geometry to region of interest geometry.
Figure 15:
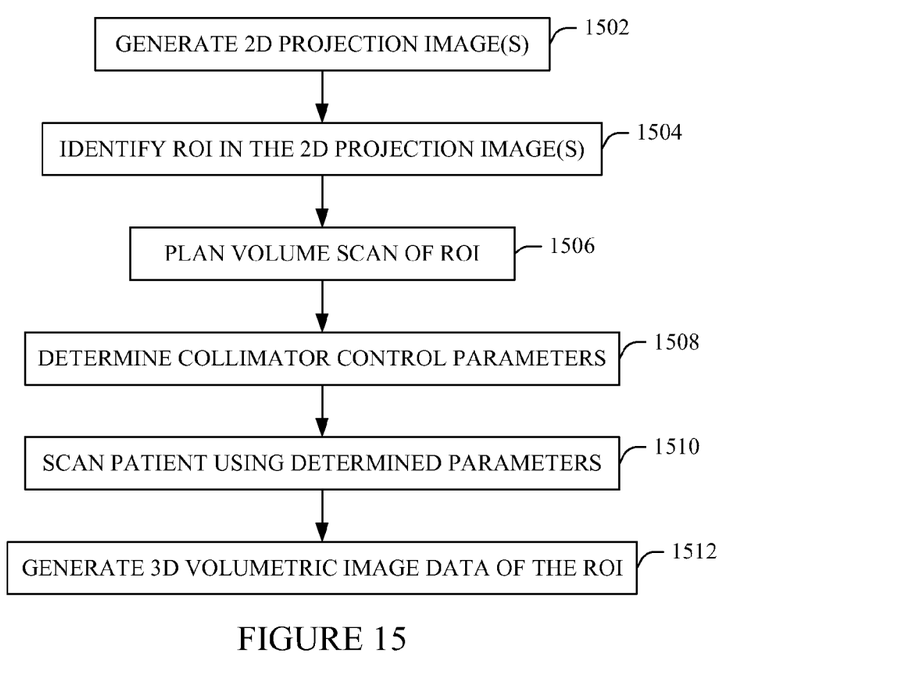
Figure 16:
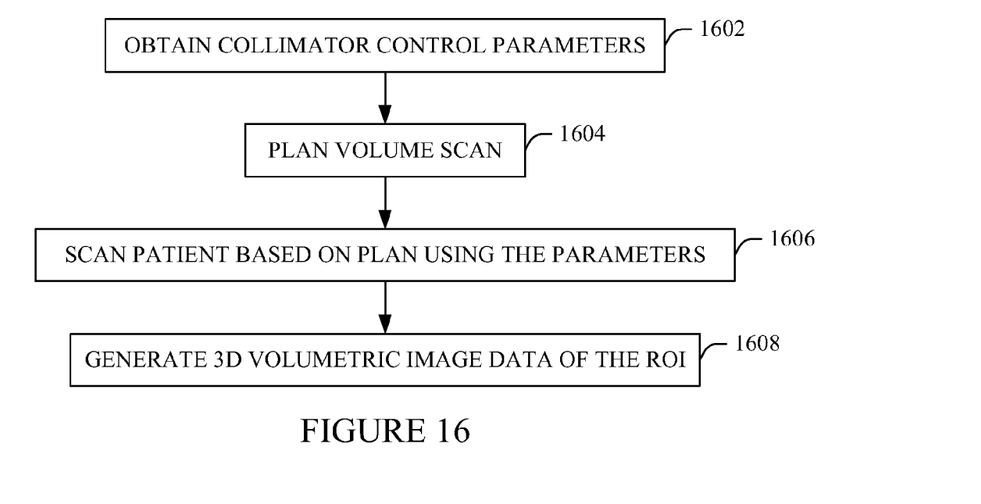

FIGS. 14, 15 and 16 illustrate various methods for collimating the radiation beam 712 to that its geometry and/or location tracks a geometry and/or location of a ROI of a patient.

It is to be appreciated that the ordering of the below acts is for explanatory purposes and not limiting. As such, other orderings are also contemplated herein. In addition, one or more of the acts may be omitted and/or one or more other acts may be included.

Initially referring to FIG. 14, at 1402 one or more 2D projection scans are performed on a patient. Where multiple 2D projection scans are preformed, the scan can be in a similar or different planes (e.g., axial, sagittal, and/or coronal).

At 1404, the acquired data is reconstructed, generating one or more 2D projection images.

At 1406, a ROI is identified in at least one of the one or more 2D projection images. It is to be appreciated that this can be done manually by a user using various segmentation tools (e.g., free hand draw, pre-defined geometrical shapes, etc.) provided in executing segmentation software and/or automatically via the executing segmentation software.

At 1408, a start scan location and either a stop scan location or a scan extent are identified for the at least one of the one or more 2D projection images. Similar to the ROI, this can be done manually and/or automatically.

At 1410, a set of collimator control parameters are determined based on the identified ROI and the one or more 2D projection images. As described herein, the set of collimator control parameters cause the collimator to produce and dynamically adjust, during scanning in the x and/or z directions, a geometry and/or location of the radiation beam to track a geometry and/or location of the ROI.

At 1412, the patient is scanned using the set of parameters to control the collimator and hence the geometry of the radiation beam.

At 1414, the acquired data is reconstructed, producing 3D volumetric image data indicative of the ROI.

At 1416, the image data is variously processed. As described herein, this may include combining and/or comparing the image data with image data from a previous study, visually displaying the data, filming the data, etc.

Turning to FIG. 15, at 1502 one or more 2D projection images for a patient are obtained. As discussed herein, these projection images can be stored images generated in connection with a previously performed imaging study.

At 1504, a ROI is identified in at least one of the one or more 2D projection images.

At 1506, a start scan location and either a stop scan location or a scan extent are identified for the at least one of the one or more 2D projection images.

At 1508, a set of collimator control parameters are generated based on the identified ROI and the one or more 2D projection images.

At 1510, the patient is scanned using the set of parameters to control the collimator and hence the geometry of the radiation beam.

At 1512, the acquired data is reconstructed, producing 3D volumetric image data indicative of the ROI.

With respect to FIG. 16, at 1602, a set of collimator control parameters that were previously determined for an ROI of a patient are obtained. As described herein, the set can be obtained from computer memory.

At 1604 the set of parameters is used to plan a subsequent volume scan of the patent. As described herein, this can be done using a newly acquired or previously acquired 2D projection image.

At 1606, the patient is scanned based on the plan.

At 1608, the acquired data is reconstructed, producing 3D volumetric image data indicative of the ROI.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
performing a three dimensional volume scan of a region of interest located in a portion of an object or subject in an examination region, including
determining a set of collimator control parameters based on one or more two dimensional projection images including data indicative of the region of interest; and
employing the set of collimator control parameters to control a collimator collimating the radiation beam to dynamically collimate the radiation beam so that a geometry and/or location of the radiation beam tracks to a geometry and/or location of the region of interest, wherein the region of interest is a sub-region of the portion of the object or subject in the examination region.

2. The method of claim 1, wherein the geometry of the radiation beam is a first geometry at a first view angle of the scan and a different geometry at a different view angle of the scan.

3. The method of claim 1, wherein substantially all of rays of the radiation beam only traverse the portion of the object or subject along paths that traverse the region of interest.

4. The method of claim 1, wherein substantially none of rays of the radiation beam traverse the portion of the object or subject along paths that do not traverse the region of interest.

5. The method of claim 1, wherein for each view angle, the region of interest is irradiated and at least part of the portion of the object or subject is not irradiated.

6. The method of claim 1, wherein outer rays of the radiation beam traverse paths that traverse a perimeter of the region of interest.

7. The method of claim 6, wherein outer rays of the radiation beam traverse paths that traverse a pre-determined margin about the perimeter of the region of interest, wherein the margin is such that the radiation beam does not traverse the entire portion of the object or subject.

8. The method of claim 1, further comprising:
adjusting the collimation along a transverse direction of the collimator.

9. The method of claim 1, further comprising:
adjusting the collimation along a longitudinal direction of the collimator.

10. The method of claim 8, wherein adjusting the collimation includes adjusting a size of a collimation aperture.

11. The method of claim 8, wherein adjusting the collimation includes adjusting a position of the collimator with respect to the radiation.

12. The method of claim 8, wherein adjusting the collimation includes adjusting a position of the collimator to track a periodically moving structure of the subject or object based on a signal indicative of a movement of the periodically moving anatomy.

13. An imaging system, comprising:
a radiation source that emits radiation in a direction towards an examination region;

a collimator having at least one collimating member that collimates the emitted radiation, producing a radiation beam having a predetermined shape and that traverses the examination region, a collimator control parameter determiner that determines collimator control parameters based on a two dimensional projection image that includes a representation of the region of interest wherein the collimator control parameters cause the at least one collimating member to physically move to dynamically adjusts a geometry and/or location of the radiation beam for one or more view angles in accordance with a geometry and/or location of a region of interest in a portion of an object or subject disposed in the examination region, wherein the region of interest is a sub-region of the portion of the object or subject disposed in the examination region; and a detector array, located opposite the source and across the examination region, that detects radiation traversing the examination region and generates a signal indicative of the detected radiation.

14. The system of claim 13, wherein substantially all of rays of the radiation beam only traverse the portion of the object or subject along paths that traverse the region of interest.

15. The system of claim 13, wherein substantially none of rays of the radiation beam traverse the portion of the object or subject along paths that do not traverse the region of interest.

16. The system of claim 13, wherein for each view angle, the region of interest is irradiated and a first sub-region of a remainder of the portion of the object or subject in the examination region is not irradiated, wherein the first sub-region is less than the remainder.

17. The system of claim 16, wherein only a second sub-region of the remainder of the portion of the object or subject in the examination region is irradiated, wherein the first and second sub-regions are different sub-regions.

18. A method for optimizing dose in an imaging examination, comprising:

identifying a region of interest of object or subject to scan in a two dimensional projection image of the object or subject;

collimating emitted radiation so that radiation traversing the examination region substantially only irradiates the region of interest while not irradiating a remainder portion of the object or subject; and adjusting the collimation as needed so that the radiation continues to substantially only irradiate the region of interest while not irradiating the remainder portion for the imaging examination.

* * * * *